(12) United States Patent
Hawkins et al.

(10) Patent No.: US 10,952,947 B2
(45) Date of Patent: *Mar. 23, 2021

(54) THICKENED CATALYZED DYE SYSTEM

(71) Applicant: ELC MANAGEMENT LLC, Melville, NY (US)

(72) Inventors: Geoffrey Hawkins, Yardley, PA (US); Daniel Thomas Nowlan, III, Hugo, MN (US)

(73) Assignee: ELC Management LLC, Melville, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/365,240

(22) Filed: Mar. 26, 2019

(65) Prior Publication Data
US 2019/0298632 A1 Oct. 3, 2019

Related U.S. Application Data

(60) Provisional application No. 62/648,601, filed on Mar. 27, 2018.

(51) Int. Cl.
| *A61Q 5/10* | (2006.01) |
| *A61K 8/44* | (2006.01) |
| *A61K 8/41* | (2006.01) |
| *A61K 8/22* | (2006.01) |

(52) U.S. Cl.
CPC .................. *A61K 8/44* (2013.01); *A61K 8/22* (2013.01); *A61K 8/415* (2013.01); *A61Q 5/10* (2013.01); *A61K 2800/30* (2013.01); *A61K 2800/4324* (2013.01); *A61K 2800/592* (2013.01); *A61K 2800/805* (2013.01)

(58) Field of Classification Search
CPC ........ A61Q 5/10; A61K 8/411; A61K 8/4926; A61K 8/415; A61K 8/22; A61K 2800/4324; A61K 8/347; A61K 8/27; A61K 8/28; A61K 33/40; A61K 9/501; A61K 2800/621
USPC .................................................... 8/405, 406
See application file for complete search history.

(56) References Cited

U.S. PATENT DOCUMENTS

| 6,106,578 | A | 8/2000 | Jones |
| 8,535,391 | B2 | 9/2013 | Blackburn et al. |
| 9,872,822 | B2 | 1/2018 | Lagrange et al. |
| 2004/0148712 | A1 | 8/2004 | Pruche et al. |

(Continued)

FOREIGN PATENT DOCUMENTS

| WO | WO-2011/000892 | 1/2011 |
| WO | WO-2012/175683 | 12/2012 |

OTHER PUBLICATIONS

PCT International Search Report; International Application No. PCT/US2019/024226; Completion Date: Jul. 8, 2019; dated Jul. 8, 2019.

(Continued)

*Primary Examiner* — Eisa B Elhilo
(74) *Attorney, Agent, or Firm* — Idris N. McKelvey (57) ABSTRACT

The invention relates to a hair dye system. The hair dye system includes at least one dye precursor, an oxidizing agent, and a catalyst. The catalyst is a homogeneous catalyst or a heterogeneous catalyst and the dye system has a viscosity of less than about 2,500 mPa-s, when measured at a shear rate of about 25 $s^{-1}$ and at about 25° C.

9 Claims, 6 Drawing Sheets

(56) References Cited

U.S. PATENT DOCUMENTS

2012/0110751 A1* 5/2012 Blackburn .............. A61K 8/19
                                                            8/421
2016/0143826 A1   5/2016 Lagrange et al.

OTHER PUBLICATIONS

PCT International Search Report; International Application No. PCT/US2019/024237; Completion Date: Jul. 10, 2019; dated Jul. 10, 2019.
PCT International Search Report; International Application No. PCT/US2019/024240; Completion Date: Jul. 10, 2019 ; dated Jul. 10, 2019.
PCT Written Opinion Of the International Searching Authority; International Application No. PCT/US2019/024226; Completion Date: Jul. 8, 2019; dated Jul. 8, 2019.
PCT Written Opinion Of the International Searching Authority; International Application No. PCT/US2019/024237, Completion Date: Jul. 10, 2019; dated Jul. 10, 2019.
PCT Written Opinion Of the International Searching Authority; International Application No. PCT/US2019/024240; Completion Date: Jul. 10, 2019 ; dated Jul. 10, 2019.

* cited by examiner

THICKENED CATALYZED DYE SYSTEM

FIELD OF THE INVENTION

The present invention relates to catalyzed hair dyeing systems and methods which may reduce the time of exposure of hair to oxidative dye treatments, thereby reducing overall hair damage from the dyeing process.

BACKGROUND OF THE INVENTION

Coloring of hair has become an increasingly popular practice. People desire hair coloration for reasons spanning from style choices to achieving more youthful appearances. As people age, the production of melanin slows, resulting in hair greying. Melanin can be purposely altered by chemical treatments to give lighter shades. The lightening is achieved by oxidizing the melanin pigments, usually with an oxidizing agent in alkaline solution, also called bleaches. Examples of oxidizing agents that can be used are hydrogen peroxide, potassium, sodium or ammonium salts of perborate or percarbonate, persulfate and percarbamide.

Bleaches are also used during oxidative dyeing treatments. Oxidative (or "permanent") dye compositions comprise "precursor dyes" which are small molecules capable of diffusing into the hair. These molecules mainly belong to three classes of aromatic compounds: diamines, aminophenols and phenols. They are sufficiently small to diffuse in the hair shaft where, once activated by an oxidizing agent such as hydrogen peroxide, they further react with other precursors to form larger colored complexes. Oxidative hair dye compositions commonly contain, in addition to the dye precursors and a source of peroxide, a variety of additional cosmetic and peroxide stabilizing agents.

Oxidizing agents can activate oxidative dye precursors across a range of pH. However, it is known that enhanced dye oxidation can be achieved via the use of a hair-swelling agent (HSA) that can adjust the pH of the oxidizing solution. Such HSA's further enhance the oxidizing and dyeing process by swelling the hair fibers to aid both the diffusion of the peroxide and dyeing agents into the hair and enabling faster, more thorough dye oxidization and hair dyeing. Preferred hair-swelling agents for adjusting the pH of peroxide hair oxidizing compositions are aqueous alkaline solutions containing ammonia (ammonium hydroxide) or monoethanolamine (MEA).

Low levels of chelants are routinely used as stabilizers or preservatives in various oxidizing compositions. For example, EDTA (ethylenediaminetetraacetic acid) is commonly used as a stabilizer in hydrogen peroxide solution, which would otherwise decompose too rapidly and could not be stored for a long time. Ethylene diaminedissucinnic acid (EDDS) is also known as a good stabilizing agent component to increase the stability of laundry bleaching products. Amounts as low as 0.1% by weight of the oxidizing composition are usually used to stabilize the oxidizing agent contained in the oxidizing compositions.

Oxidative treatments of hair such as bleaching (decoloration) and oxidative dyeing give good results and are very commonly used. They are however not without drawbacks. The oxidizing agents used for bleaching and oxidative dyeing damage hair, to some extent. The mechanism by which damage is caused to the hair fibers is not perfectly understood. However, it is known that some of the disulphide bonds linking the keratin chains break in the presence of oxidizing compositions. Repeated oxidative treatments leave weak, brittle hairs, which have little shine and luster. An enormous effort has been made to address this problem, and various solutions have been proposed.

Today, most dyeing or bleaching compositions are sold with a conditioner, which is applied on hair after the bleaching or dyeing composition has been rinsed off. Examples of conditioning agents are silicones, cationic surfactants and cationic polymers. However efficient, conditioners cannot prevent successive chemical treatments causing premature hair breakage. In fact, conditioners do not bring the hair back to its initial condition but merely conceal the damage under a protective layer of the conditioning agent, which only results in an improved feel of the hair.

U.S. Pat. No. 7,686,849 to Forbes et al. addresses the use of organotitanates as catalysts for oxidative hair color. The patent acknowledges that these organotitanate catalyst are prone to hydrolysis, offering hydrolysis as the reasoning and mechanism for organotitanates acting as bonding agents. The high pH instability of organotitanates is known in the literature, academic as well as vendor, and it is fully expected that these catalysts will hydrolyze under high pH formulation conditions to make titanium dioxide.

There is an ongoing need to provide hair color with a stabilized approach for minimizing or reducing hair damage in an oxidative hair dye system.

SUMMARY OF THE INVENTION

The present invention relates to a hair dye system. The hair dye system includes at least one dye precursor, an oxidizing agent, and a catalyst. The catalyst is a homogeneous catalyst or a heterogeneous catalyst and the dye system has a viscosity of less than about 2,500 mPa-s, when measured at a shear rate of about 25 $s^{-1}$ and at about 25° C.

The present invention further relates to methods for making and using the dye system.

DETAILED DESCRIPTION OF THE INVENTION

Dye Precursor Compounds

The following conventional primary intermediate and coupler substances may be used as the oxidation dye precursor compounds.

As primary intermediate substances the following can be used: standard primary aromatic amines with an additional free or substituted hydroxy or amino group substituent in the ortho- or para-position, indole derivative compounds or substituted heterocyclic compounds, especially from the classes of pyrimidines and pyrazoles, such as 1,4-diaminobenzene (p-phenylenediamine), 1,4-diamino-2-methylbenzene (p-toluene-diamine), 1,4-diamino-2,6-dimethylbenzene, 1,4-diamino-2,5-dimethylbenzene, 1,4-diamino-2,3-dimethylbenzene, 1,4-diamino-2-chlorobenzene, 4-di(2-hydroxyethyl)amino aniline, N,N-bis-(2-hydroxyethyl)-p-phenylenediamine, 4-(2-methoxyethyl)amino aniline, 1,4-diamino-2-(2-hydroxy-ethyl)-benzene, 1,3-bis-N-(2-hydroxy-ethyl)-N-(4-amino-phenyl)-amino-2-propanol, 2',2-1,2-ethanediyl-bis(oxy-2,1-ethanediyloxy)-bis-1,4-diaminobenzene, 4-amino-phenol, 4-amino-3-methylphenol, 4-amino-2-(aminomethyl)phenol, 4-methylaminophenol, 4-amino-2-(2-hydroxyethyl)amino-methylphenol, 4-amino-2-(methoxymethyl)-phenol, 5-amino-salicylic acid, 2,4,5,6-tetraaminopyrimidine, 2,5,6-tri-amino-4-hydroxy-pyrimidine, 4,5-diamino-1-(2-hydroxyethyl)-1H-pyrazole, 4,5-diamino-1-(1-methylethyl)-1H-pyrazole, 4,5-diamino-1-(4-methylphenyl)methyl-1H-pyrazole, 4,5-diamino-1-(4-chloro-phenyl)methyl-1H-pyrazole, 4,5-diamino-1-methylpyrazole, 2,5-dimethylpyridine, 2-amino-6-methylphenol or 2-amino-5-methyl-phenol, alone or in combination with each other.

Suitable coupler substances include, for example, substituted m-diaminobenzenes, m-aminophenol, resorcinol derivative compounds, indole derivative compounds, naphthols or substituted heterocyclic compounds can be used, especially from the classes of pyrimidines and pyridines, such as N,N-dimethyl-3-ureidoaniline, 2,6-diamino-pyridine, 2-amino-4-(2-hydroxyethyl)amino anisole, 2,4-diamino-1-fluoro-5-methyl-benzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di-(2-hydroxyethyl)amino-1,5-dimethoxy-benzene, 2,3-di-amino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxyethoxy)-benzene, 3-di-(2-hydroxyethyl)-amino aniline, 4-amino-1-ethoxy-2-di-(2-hydroxyethyl)amino-benzene, 5-methyl-2-(1-methylethyl) phenol, 3-(2-hydroxy-ethyl)amino aniline, 3-(2-aminoethyl) amino aniline, 1,3-di-(2,4-diaminophenoxy)propane, 2,4-dimethoxy-1,3-diamino-benzene, 2,6-bis-(2-hydroxyethyl) aminotoluene, 3-dimethyl-aminophenol, 5-amino-2-methyl-phenol, 5-amino-4-fluoro-2-methylphenol, 5-amino-4-methoxy-2-methyl-phenol, 5-amino-4-ethoxy-2-methyl-phenol, 3-amino-2,4-dichlorophenol, 3-diethylaminophenol, 3-amino-2-chloro-6-methyl-phenol, 3-aminophenol, 3-(amidomethyl)aminophenol, 5-(2-hydroxy-ethyl)amino-2-methyl-phenol, 3-(2-Hydroxyethyl) amino-phenol, 5-amino-2-ethylphenol, 5-(3-hydroxypropyl) amino-2-methylphenol, 3-(2,3-dihydroxypropyl)amino-2-methyl-phenol, 3-(2-hydroxy-ethyl)amino-2-methylphenol, 5-(2-hydroxyethyl)amino-1,3-benzodioxole, 1,3-dihydroxybenzene, 4-chloro-1,3-dihydroxybenzene, 1,3-dihydroxy-2-methyl-benzene, 3,4-methylenedioxybenzene, 3,4-methylenedioxyaniline, 1-hydroxy-6-bromo-3,4-methylenedioxybenzene, 5-amino-4-chloro-2-methylphenol, 3,4-diaminobenzoic acid, 6-hydroxy-2H-1,4-benzoxazine, 2,7-dihydroxynaphthalene, 1-naphthol, 1,7-dihydroxynaphthalene, 1,5-dihydroxynaphthalene, 2,6-dihydroxy-4-methylpyridine, 2,6-dihydroxypyridine, 2-methyl-1-naphthol acetate, phenylmethylpyrazolone, 2,6-dihydroxy-3,4-dimethylpyridine, 4-hydroxyindole, 5,6-dihydroxyindole, 5-hydroxyindole, 6-hydroxyindole, 7-hydroxyindole, 2,3-indolidione, 2-amino-3-hydroxypyrimidine or 4,5,6-dihydroxy-indoline, alone or in combination with each other.

The composition may contain one or more of the previously named primary intermediate and coupler substances. These dye compounds, in so far as they are bases can also be used in the form of their physiologically compatible acid addition salts, for example as the hydrochlorides and/or sulfates, or, in so far as they have aromatic OH groups, in the form of salts with bases, for example as alkali phenolates.

The oxidation dye pre-cursor compounds are, based on the ready-to-use dye mixture, contained in the oxidation dye composition according to the invention in a total amount of from 0.001 to 20 percent by weight, preferably in a total amount of from 0.01 to 5 percent by weight of the dye system. The primary intermediate and coupler substances are preferably used in equimolar amounts. It is however not disadvantageous when one of these classes of substances is present in excess with respect to the other, or vice versa. The primary intermediate and coupler substance can be present, for example, in a ratio of from about 1:0.5 to about 1:2.

Oxidizing Agent

The present invention includes an oxidizing agent. Exemplary oxidizing agents include, for example, percarbonates, persulfates, organic peracids and organic hydroperoxides. In certain circumstances, molecular oxygen (including air) may also be used. According to the present invention, a preferred oxidizing agent is hydrogen peroxide. In one embodiment, the oxidizing agent may be present at a level of from about 0.75 to about 6 percent by weight of the dye system.

Dye Catalyst

The present invention includes at least one metal-containing compound for use as a catalyst. The metal-containing compound preferably comprises at least one inorganic metal compound. Preferred inorganic metal compounds comprise compounds of d-block transition metals such as scandium, titanium, vanadium, chromium, molybdenum, iron, manganese, cobalt, nickel, copper, zirconium and zinc including, but not limited to, the acetates, acetylacetonates, aluminates, bicarbonates, borates, bromates, carbonates, chlorites, cyanides, diethylcitrates, halides, hexafluoroacetylacetonates, hexafluorophosphates, hexafluorosilicates, dihydrogen phosphates, hydrogen carbonates, hydrogen sulfates, hydrogen sulfides, hydrogen sulfites, hydroxides, hypochlorites, iodates, nitrates, nitrites, oxalates, oxides, perfluorophthalocyanines, peroxides, phosphates, phthalocyanines, pyrophosphates, silicates, sulfamates, sulfates, sulfides, sulfites, tartrates, tetrafluoroborates, thiocyanates, thiolates, thiosulfates, tosylates and triflates of these metals.

Particularly preferred compounds in this context include $VBr_3$, $VCl_2$, $VCl_3$, $VCl_4$, $V_2O_3$, $V_2O_4$, $V_2O_5$, $VO(SO_4)$, $VOCl_3$, $VOF_3$, $V(C_5H_7O_2)_3$, $VO(C_5H_7O_2)_2$, $VO(OR)_3$, $Mo_2(OCOCH_3)_4$, $Mo(CO)_6$, $MoCl_3$, $MoCl_5$, $MoO_2Cl_2$, $MoF_6$, $MoO_2$, $MoO_3$, $MoS_2$, $MoOCl_4$, $MoSO_4$, $Mn(OCOCH_3)_2$, $Mn(OCOCH_3)_2.xH_2O$, $Mn(C_5H_7O_2)_2$, $MnBr_2$, $MnBr_2.xH_2O$, $MnCO_3$, $MnCO_3.xH_2O$, $Mn_2(CO)_{10}$, $MnCl_2$, $MnCl_2.xH_2O$, $MnF_2$, $MnF_3$, $Mn(HCO_2)_2.xH_2O$, $MnI_2$, $Mn(NO_3)_2$, $Mn(NO_3)_2.xH_2O$, $Mn_3O_4$, $Mn_2O_3$, $MnO_2$, Mn($C_3$2$H_{16}N_8$), MnSO$_4$, MnSO$_4$.xH$_2$O, MnS, Fe(OCOCH$_3$)$_2$, Fe(OCOCH$_3$)$_3$, FeBr$_2$, FeBr$_3$, FeCl$_2$, FeCl$_2$.xH$_2$O, FeCl$_3$, FeCl$_3$.xH$_2$O, Fe(OEt)$_3$, FeSO$_4$.NH$_3$CH$_2$CH$_2$NH$_3$SO$_4$.4H$_2$O, Fe4[Fe(CN)$_6$]3, FeF$_2$, FeF$_3$, FeF$_3$.xH$_2$O, FeI$_2$, Fe(CH$_3$CHOHCOO)$_2$.xH$_2$O, Fe(NO$_3$)$_3$.xH$_2$O, Fe(C$_2$O$_4$).xH$_2$O, FeO, Fe$_2$O$_3$, Fe$_3$O$_4$, FePO$_4$.xH$_2$O, Fe(C$_{32}$H$_{16}$N$_8$), FeSO$_4$.xH$_2$O, FeS, Fe(BF$_4$)$_4$.xH$_2$O, Fe(SCN)$_2$, Co(OCOCH$_3$)$_2$, Co(OCOCH$_3$)$_2$.xH$_2$O, Co(C$_5$H$_7$O$_2$)$_2$, Co(C$_5$H$_7$O$_2$)$_2$.xH$_2$O, Al$_2$CoO$_4$, CoBr$_2$, CoBr$_2$.xH$_2$O, CoCO$_3$, CoCO$_3$.xH$_2$O. Co$_2$(CO)s, CoCl$_2$, CoCl$_2$.xH$_2$O, CoF$_2$, Co[CH$_3$(CH$_2$)$_3$CH(C$_2$H$_5$)CO$_2$]$_2$, Co(OH)$_2$, CoI$_2$, Co(NO$_3$)$_2$, Co(NO$_3$)$_2$.xH$_2$O, Co(O$_2$O$_4$), Co(C$_2$O$_4$).xH$_2$O, CoSO$_4$, CoSO$_4$.xH$_2$O, Co(BF$_4$)$_2$, Co(BF$_4$)$_2$.xH$_2$O, Co(SCN)$_2$, Ni(OCOCH$_3$)$_2$, Ni(OCOCH$_3$).xH$_2$O, Ni(C$_5$H$_7$O$_2$)$_2$, NiBr$_2$, NiBr$_2$.xH$_2$O, NiCO$_3$, Ni(CO$_3$).xNi(OH)$_2$, NiCl$_2$, NiCl$_2$.xH$_2$O, NiOCoO, Ni[CH$_3$(CH$_2$)$_3$CH(C$_2$H$_5$)CO$_2$]2, NiF$_2$, Ni(OH)$_2$, NiI$_2$, Ni(NO$_3$)$_2$, Ni(NO$_3$)$_2$.xH$_2$O, Ni(C$_2$O$_4$), Ni(C$_2$O$_4$).xH$_2$O, NiO$_2$, NiO$_2$.xH$_2$O, Ni(C$_{32}$H$_{16}$N$_8$), Ni(SO$_3$NH$_2$)$_2$, Ni(SO$_3$NH$_2$)$_2$.xH$_2$O, NiSO$_4$, NiSO$_4$.xH$_2$O, Ni$_3$S$_2$, NiZnFe$_4$O$_4$, CuOCOCH$_3$, Cu(OCOCH$_3$)$_2$, Cu(OCOCH$_3$)$_2$.xH$_2$O, Cu(C$_5$H$_7$O$_2$)$_2$, CuBr, CuBr$_2$, CuCO$_3$, CuCO$_3$.Cu(OH)$_2$, CuCl, CuCl$_2$, CuCl$_2$.xH$_2$O, Cu[CH$_3$(CH$_2$)$_3$CH(C$_2$H$_5$)CO$_2$]$_2$, CuF$_2$, CuF$_2$.xH$_2$O, Cu(HCO$_2$)$_2$, Cu(HCO$_2$)$_2$.xH$_2$O, Cu(OH)$_2$, Cu$_2$(OH)PO$_4$, CuI, CuFe$_2$O$_4$, Cu(NO$_3$)$_2$, Cu(NO$_3$)$_2$.xH$_2$O, Cu$_2$O, CuO, Cu(C$_{32}$H$_{16}$N$_8$), Cu$_2$P$_2$O$_7$.xH$_2$O, CuSO$_4$, CuSO$_4$.xH$_2$O, CuS, Cu[O$_2$CCH(OH)CH(OH)CO$_2$].xH$_2$O, Cu(BF$_4$)$_2$, Cu(BF$_4$).xH$_2$O, Cu(SCN), Zn(OCOCH$_3$)$_2$, Zn(OCOCH$_3$)$_2$.xH$_2$O, Zn(C$_5$H$_7$O$_2$)$_2$, Zn(C$_5$H$_7$O$_2$)$_2$.xH$_2$O, ZnBr$_2$, ZnBr$_2$.xH$_2$O, ZnCl$_2$, ZnF$_2$, Zn(C$_{32}$F$_{16}$N$_8$), Zn(C$_5$HF$_6$O$_2$)$_2$, Zn(C$_5$HF$_6$O$_2$)$_2$.xH$_2$O, ZnSiF$_6$.xH$_2$O, ZnI$_2$, ZnFe$_2$O$_4$, Zn(NO$_3$)$_2$, Zn(NO$_3$)$_2$.xH$_2$O, Zn(C$_2$O$_4$), Zn(C$_2$O$_4$).xH$_2$O, ZnO, ZnO.xH$_2$O, ZnO$_2$, Zn$_3$(PO$_4$)$_2$, Zn(C$_{32}$H$_{16}$N$_8$), ZnSO$_4$, ZnSO$_4$.xH$_2$O, ZnS, Zn(BF$_4$)$_2$, Zn(BF$_4$)$_2$.xH$_2$O, Zr(OCOCH$_3$)$_4$, Zr(OCOCH$_3$)x(OH)$_{4-x}$, Zr(C$_5$H$_7$O$_2$)$_4$, Zr(C$_{26}$H$_{44}$O$_{16}$), ZrCO$_3$(OH)$_2$.ZrO$_2$, ZrCl$_4$, ZrF$_4$, ZrF$_4$.xH$_2$O, Zr(HPO$_4$)$_2$, Zr(OH)$_4$, ZrI$_4$, ZrO(NO$_3$)$_2$, ZrO(NO$_3$)$_2$.xH$_2$O, Zr(SO$_4$)$_2$, Zr(SO$_4$)$_2$.xH$_2$O, ZrOCl$_2$ and ZrOCl$_2$.xH$_2$O. These compounds may, for example, be applied in combination with readily available amino phenolic compounds, such as p- or m-aminophenol, and oxidizing agents such as hydrogen peroxide.

Alternative metal compounds for use as catalysts comprise salts of the alkali metals of Group 1, such as potassium, or the alkaline earth metals of Group 2, for example magnesium. Specific examples of suitable salts include acetates, acetylacetonates, aluminates, bicarbonates, borates, bromates, carbonates, chlorites, cyanides, diethylcitrates, halides, hexafluoroacetylacetonates, hexafluorophosphates, hexafluorosilicates, dihydrogen phosphates, hydrogen carbonates, hydrogen sulfates, hydrogen sulfides, hydrogen sulfites, hydroxides, hypochlorites, iodates, nitrates, nitrites, oxalates, oxides, perfluorophthalocyanines, peroxides, phosphates, phthalocyanines, pyrophosphates, silicates, sulfamates, sulfates, sulfides, sulfites, tartrates, tetrafluoroborates, thiocyanates, thiolates, thiosulfates, tosylates and triflates, such as KAl(SO$_4$)$_2$K$_2$CO$_3$, K$_3$PO$_4$, KNO$_3$, KCl, MgSO$_4$, Mg$_3$(PO$_4$)$_2$, MgCO$_3$, Mg(NO$_3$)$_2$ and MgCl$_2$.

In certain embodiments of the invention wherein the at least one metal-containing compound comprises at least one inorganic metal compound, the catalyst may comprise at least one mineral or clay. Preferred examples of the minerals or clays include anatase, brookite, eudialyte, ilmenite, perovskite, rutile, sabaite, zircon, zirconolite, zircohylite or zirkelite.

When applying the dye systems to hair fibers, it is preferred that the at least one metal-containing compound for use as a catalyst comprises at least one metal complex comprising at least one organic ligand. It is also preferred that the at least one dye precursor comprises an aromatic amino compound, a phenolic compound or an amino phenolic compound such as p- or m-aminophenol, and that the oxidizing agent is hydrogen peroxide.

In the context of the present invention, particularly suitable catalysts which comprise at least one metal complex comprising at least one organic ligand are metal chelates, most particularly zirconium complexes comprising at least one organic ligand. Typical ligands include optionally substituted alkyl ligands. A particularly preferred example of such a catalyst is aluminum zirconium glycinate (AZG) chelate complex.

AZG is particularly preferred relative to titanium-based metal compounds. Both zirconium and titanium are known to undergo hydrolytic polymerization (known as olation) to form large molecular weight oligomers. In the case of aluminum zirconium chlorohydrates and glycinates this reaction does not substantially affect catalytic reactivity nor does it fundamentally alter the structure of the material. In contrast organotitanates are structurally modified in this environment to form titanium oxide which is catalytically inactive under these conditions. Accordingly, in one embodiment, the dye catalyst is free of titanium. And in a further embodiment, the compositions of the present invention are free of titanium.

The dye catalyst may be present at a level of from about 0.0001 to 20% by weight of the dye system.

Alkalizer

The present invention may also include an alkalizer. Suitable alkalizers include, for example, alkanolamines such as aminomethylpropanol (AMP) and monoethanolamine (MEA). A particularly preferred alkalizer is ammonia.

Alkalizers are known in the art of dying hair for the purpose of raising the cuticle of the hair to facilitate delivery of dye compounds below the cuticle. While efforts have been undertaken to avoid ammonia, primarily, due to its smell and perception of hair damage, it has been found that the combination of an alkalizer with the catalyst, herein, increases the rate of reaction and may therefore reduce hair damage.

It has also been found that the present invention functions advantageously at a pH of about 9 or greater. Therefore, the alkalizer herein may be used as a pH adjuster, to facilitate a pH at or above about 9. Preferably, the pH of the present invention is from about 9 to about 10.

Preferably, the alkalizer may be present at a level of from about 0.1 to 25 percent by weight of the dye system.

Figure 1:
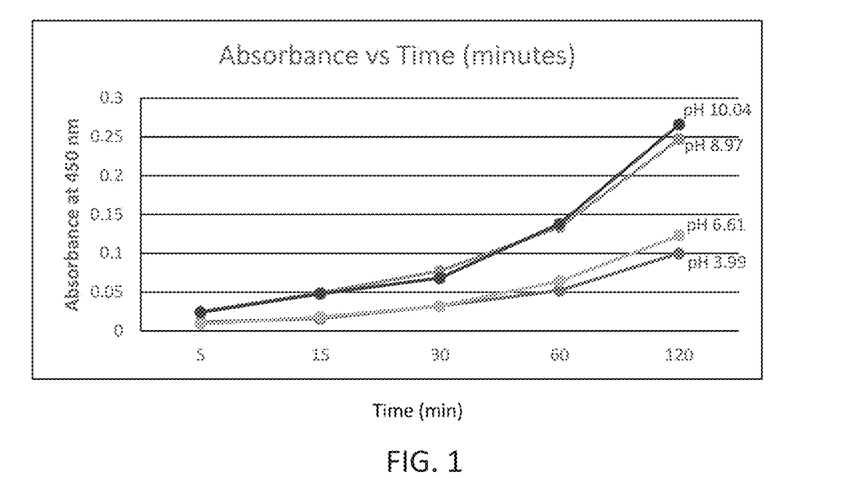
FIG. 1 shows the rates of reaction of the dye system herein at varying pH levels.

FIG. 1 shows the rates of reaction of the dye system herein at varying pH levels. The self-coupling reaction of m-aminophenol (3.0 mmol) mediated by hydrogen peroxide (5 eq) in water (20 mL) was monitored by UV-vis spectroscopy at various pH values (adjusted with HCl or NH$_4$OH) in the presence of 5 mol % aluminum zirconium pentachlorohydrex (Rezal 67, SummitReheis). The rates of absorption are directly proportional to the pH of the dye system, including the catalyst herein. For example, at pH 8.97 (about pH 9), the rate of absorption is more than double the rate of absorption at pH levels below 6.61. Therefore, the catalyst herein operates synergistically with the pH level to determine the rate of absorption. Accordingly, at a pH level at about 9 or above, the dyeing process occurs faster than at pH levels below for example, 6.61.

Thickening Agents

Thickening agents, including thickener or gelling agents, include substances which can increase or control the viscosity of a composition. Thickeners include those that can increase the viscosity of a composition without substantially modifying the efficacy of the active ingredients within the composition. Thickeners can also increase the stability of compositions.

Non-limiting examples of thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the cross-linking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379.

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer are hydroxyalkylated (preferably hydroxyethylated or hydroxypropylated) to form a hydroxyalkylated cellulose, which is then further modified with a $C_{10}$-$C_{30}$ straight chain or branched chain alkyl group through an ether linkage. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, chitosan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboxymethyl dextran, sodium carrageenan, tragacanth gum, xanthan gum, and mixtures thereof.

Further non-limiting examples of thickening agents include carbomer, cetyl alcohol, ammonium acryloydimethyltaurate/VP copolymer, aluminum starch actenylsuccinate, cocamidopropyl betaine, PPG-2 hydroxyethyl coco/isostearamide, tin oxide, hexadecane copolymer, calcium aluminum borosilicate, alumina, calcium sodium borosilicate, aluminum calcium sodium silicate, synthetic fluorphlogopite, dipropylene glycol, polyethylene glycol, quaternium-90 bentonite, kaolin, and disodium EDTA.

Non-Limiting Examples

The following Examples illustrate specific embodiments of the compositions of the present invention, but are not intended to be limiting thereof. Other modifications can be undertaken by the skilled artisan without departing from the spirit and scope of this invention.

The compositions illustrated in the following Examples are prepared according to the methods described hereinafter. All exemplified amounts are listed as weight percents and exclude minor materials such as diluents, preservatives, color solutions, imagery ingredients, botanicals, and so forth, unless otherwise specified.

The following are representative of dye system of the present invention:

|  | 1 | 2 | 3 | 4 | 5 | 6 | 7 | 8 |
|---|---|---|---|---|---|---|---|---|
| Phase A |  |  |  |  |  |  |  |  |
| Water | q.s. | q.s. | q.s. | q.s. | q.s. | q.s. | q.s. |  |
| Catalyst[1] | — | 2.24 | 2.24 | 2.24 | 2.24 | 2.24 | 2.24 | 2.24 |
| Jaguar S | — | — | — | — | — | — | — | 1.00 |
| Butylene glycol | — | — | — | — | — | 5.00 | — | 5.00 |
| Decyl glucoside | 5.00 | 5.00 | 5.00 | 5.00 | 5.00 | — | 5.00 |  |
| Glycerine | 2.00 | 2.00 | 2.00 | 2.00 | 2.00 | 5.00 | 2.00 | 2.00 |
| Lauramidopropyl betaine | — | — | — | — | — | 2.00 | — | — |
| Erhythorbic acid | 0.2 | 0.2 | 0.2 | 0.2 | 0.2 | 0.2 | 0.2 | 0.50 |
| Tetrasodium EDTA | 0.40 | 0.40 | 0.40 | 0.40 | 0.40 | 4.2 | 0.40 | 1.00 |
| Sodium sulfite | 0.20 | 0.20 | 0.20 | 0.20 | 0.20 | 0.20 | 0.20 | 0.50 |
| Arginine | — | — | — | — | — | 2.00 | — | — |
| p-aminophenol | 0.20 | 0.20 | 0.20 | 0.20 | — | — | — | 0.50 |
| 4-amino-2-hydroxytoluene | 0.22 | 0.22 | 0.22 | 0.22 | 1.50 | 1.50 | — | — |
| 2,4-diaminophenoxy ethanol | — | — | — | — | 1.46 | 1.46 | 0.10 | — |
| 4-amino-m-cresol | — | — | — | — | — | — | 0.30 | — |
| p-aminophenol | — | — | — | — | — | — | 0.50 |  |
| m-aminophenol | — | — | — | — | — | — | 0.60 | 0.25 |
| tetraaminopyrimidine sulfate | — | — | — | — | — | — | 0.10 | — |
| Resorcinol | — | — | — | — | — | — | 0.50 | — |

-continued

|  | 1 | 2 | 3 | 4 | 5 | 6 | 7 | 8 |
|---|---|---|---|---|---|---|---|---|
| Phase B | | | | | | | | |
| Peg-40 hydrogenated castor oil | — | — | — | — | — | 3.00 | — | — |
| Cocamide MEA | 5.00 | 5.00 | 5.00 | 5.00 | 10.00 | — | — | — |
| Glyceryl Stearate/PEG-100 Stearate[2] | — | — | — | — | — | 1.50 | — | — |
| Glyceryl Stearate | 4.00 | 4.00 | 4.00 | 4.00 | 4.00 | — | — | — |
| Cetearyl alcohol | 2.50 | 2.50 | 2.50 | 2.50 | 2.50 | 4.00 | — | — |
| Steareth-21 | 2.50 | 2.50 | 2.50 | 2.50 | 3.00 | — | — | — |
| Candellila wax | 2.00 | 2.00 | 2.00 | 2.00 | 2.00 | — | — | — |
| Oleic acid | 1.00 | 1.00 | 1.00 | 1.00 | 1.00 | 9.00 | — | — |
| Sorbitan oleate | — | — | — | — | — | 3.00 | — | — |
| Sunflower oil | — | — | — | — | — | 2.00 | — | — |
| Phase C | | | | | | | | |
| Ammonium hydroxide | 6.9 | 6.9 | 6.9 | 6.9 | 4.5 | 6.4 | — | — |
| Aminomethyl propanol | — | — | — | — | — | — | 8.7 | 8.5 |

[1]Aluminum Zirconium Glycinate, available from SummitReheis
[2]SP ARLACEL 165-MBAL-PW-(AP), available from Croda Methods for Forming the Dye System The components of the dye system may be combined according to a variety of conditions. Exemplary methods for forming the dye system are described hereinafter.

For the purpose of comparison, Example 1, provided above, illustrates a dye composition which is absent of the catalyst of the present invention. This formula may be prepared according to the following method.

Method for Formulating a Dye System without a Catalyst

Example 1 is formed according to the following method. Phase A is prepared by adding the water, decyl glucoside, and glycerine to a beaker with moderate stirring using a propeller. Once homogeneous, the erythorbic acid, tetrasodium EDTA, and sodium sulfite are added. The mixture is then heated to 80° C. At approximately 70° C. the p-aminophenol and 4-amino-2-hydroxytoluene are added with an increase in stirring rate to aid dissolution.

Phase B is prepared by weighing the components into a single beaker and heating to 80° C. on a hot plate.

Once both phases have reached 80° C. they are combined with one another and the heat is removed, allowing this system to cool.

Once the mixture has cooled to 35° C. the ammonium hydroxide of Phase C is combined with the mixture of Phases A and B, with vigorous mixing, until a thickened homogeneous emulsion is obtained. The final emulsion is then transferred to suitable containers for later use.

Methods for Forming a Dye System Including a Catalyst

Examples 2-8, herein above, are illustrative of dye systems which include a catalyst according to the present invention. Various methods for formulating such dye systems are provided hereinafter.

Method I

Example 2 is prepared according to the following method. Phase A is prepared by adding the water, decyl glucoside, and glycerine to a beaker with moderate stirring using a propeller. Once homogeneous, the erythorbic acid, tetrasodium EDTA, and sodium sulfite are added. The mixture is then heated to 80° C. At approximately 70° C. the p-aminophenol and 4-amino-2-hydroxytoluene are added with an increase in stirring rate to aid dissolution.

Phase B is prepared by weighing the components into a single beaker and heating to 80° C. on a hot plate.

Once both phases have reached 80° C. they are combined and the heat is removed, allowing this system to cool.

In this example, once the mixture has cooled to 40° C. the AZG catalyst is added to the mixture. After the mixture has further cooled to 35° C. the ammonium hydroxide of Phase C is combined with the mixture of Phases A and B, with vigorous mixing, until a thickened homogeneous emulsion is obtained. The final emulsion is then transferred to suitable containers for later use.

Method II

Example 3 is prepared according to the following method. Phase A is prepared by adding the water, decyl glucoside, and glycerine to a beaker with moderate stirring using a propeller. Once homogeneous, the erythorbic acid, tetrasodium EDTA, and sodium sulfite are added. The mixture is then heated to 80° C. In this example, at approximately 70° C. the AZG catalyst is added to the aqueous phase. This is accompanied by a change in haziness of the liquid. Once homogeneous the p-aminophenol and 4-amino-2-hydroxytoluene are added with an increase in stirring rate to aid dissolution.

Phase B is prepared by weighing the components into a single beaker and heating to 80° C. on a hot plate.

Once both phases have reached 80° C. they are combined and the heat is removed, allowing this system to cool.

Once the mixture has cooled to 35° C. the ammonium hydroxide of Phase C is combined with the mixture of Phases A and B, with vigorous mixing, until a thickened homogeneous emulsion is obtained. The final emulsion is then transferred to suitable containers for later use.

Method III

Example 4 is prepared according to the following method. Phase A is prepared by adding the water, decyl glucoside, and glycerine to a beaker with moderate stirring using a propeller. Once homogeneous, the erythorbic acid, tetrasodium EDTA, and sodium sulfite are added. The mixture is then heated to 80° C. At approximately 70° C. the p-aminophenol and 4-amino-2-hydroxytoluene are added with an increase in stirring rate to aid dissolution.

Phase B is prepared by weighing the components into a single beaker and heating to 80° C. on a hot plate.

Once both phases have reached 80° C. they are combined and the heat is removed, allowing this system to cool.

Once the mixture has cooled to 35° C. the ammonium hydroxide of Phase C is combined with the mixture of Phases A and B, with vigorous mixing, until a thickened homogeneous emulsion is obtained. Finally, the AZG catalyst is added slowly to the thickened emulsion. Once addition is complete and homogeneous the final emulsion is then transferred to suitable containers for later use.

Figure 2:
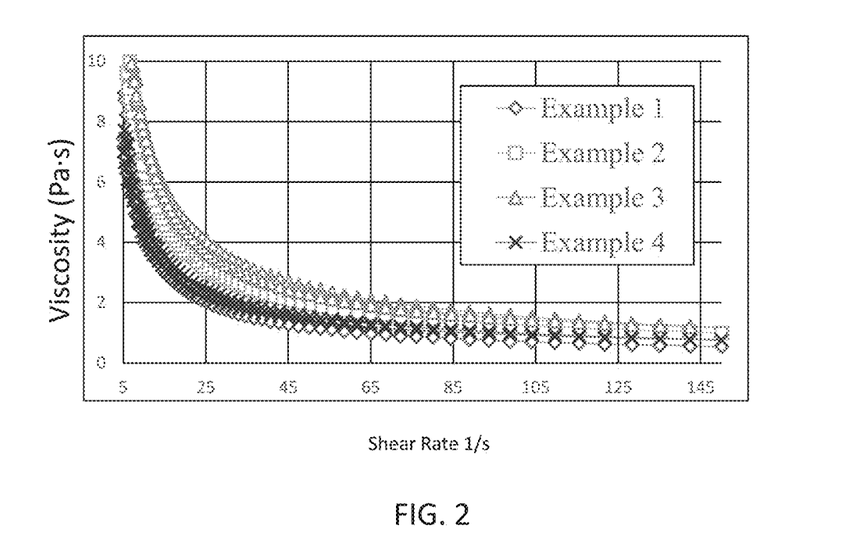
FIG. 2 is a comparative graph, illustrating changes to viscosity vs. shear rate of exemplary compositions herein.

Examples 2-4 are identical to one another regarding their overall ingredient list, but are formulated according to the discrete methods discussed hereinabove. Examples 5-8 are provided for further illustrative purposes, and may be prepared according to any of the methods described herein. Each of examples 2-4 differ from Example 1 in that Example 1 does not include a catalyst, and therefore is also formulated according to a different method. FIG. 2 illustrates the impact of addition of the catalyst to the base formula on its viscosity. According to formulation Methods I and II, the addition of the catalyst increases the overall viscosity of the dye system. These methods result in enhanced spreadability and even distribution of the catalyst system herein. However, the technique described in Method III fails to achieve the viscosity benefits of Methods I and II.

Therefore, it has been found that addition of an alkalizer, such as $NH_3$, before the catalyst is introduced, results in uneven distribution of the catalyst.

Figure 3A:
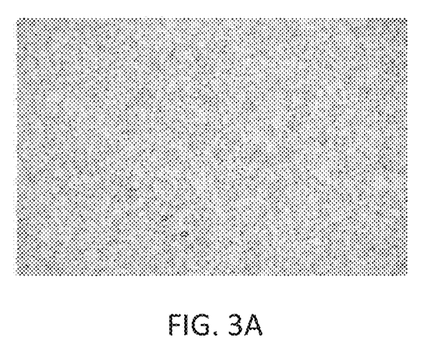
FIGS. 3A-3C show the formula of Example 1, when formulated according to Method I herein, under increasing magnification (4×, 20×, and 10×, respectively), 24 hours after formulation.
Figure 3B:
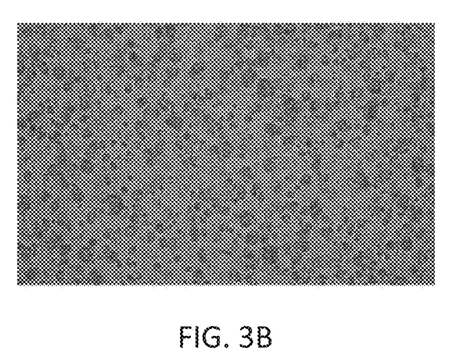
Figure 3C:
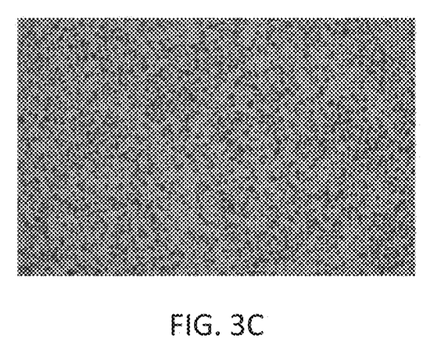

FIGS. 3A-3C show the formula of Example 1, under increasing magnification (4×, 20×, and 10×, respectively), 24 hours after formulation. The orientation of the dye structure is believed to correlate to the viscosity profile of Example 1 illustrated in FIG. 3. As the dye system thickens, the structure becomes increasingly dense.

Figure 4A:
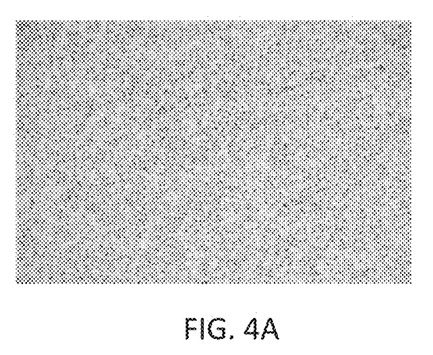
FIGS. 4A-4C show the formula of Example 2, when formulated according to Method I herein, under increasing magnification (4×, 20×, and 10×, respectively), 24 hours after formulation.
Figure 4B:
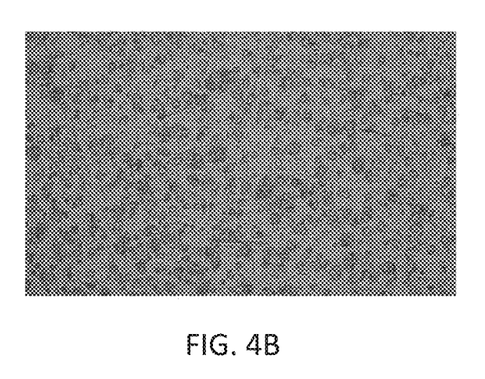
Figure 4C:
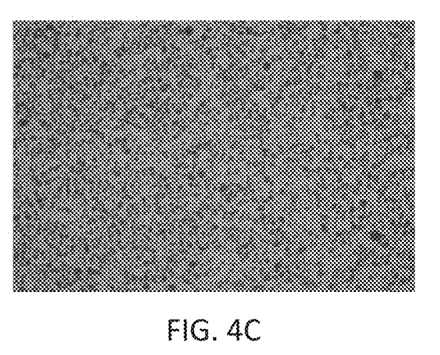

FIGS. 4A-4C show the formula of Example 2, when formulated according to Method I herein, under increasing magnification (4×, 20×, and 10×, respectively), 24 hours after formulation. As is illustrated in these depictions, the dye system is more dense, with an even distribution of the catalyst.

Figure 5A:
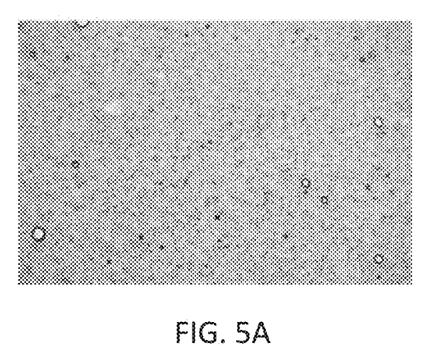
FIGS. 5A-5C show the formula of Example 3, when formulated according to Method II herein, under increasing magnification (4×, 20×, and 10×, respectively), 24 hours after formulation.
Figure 5B:
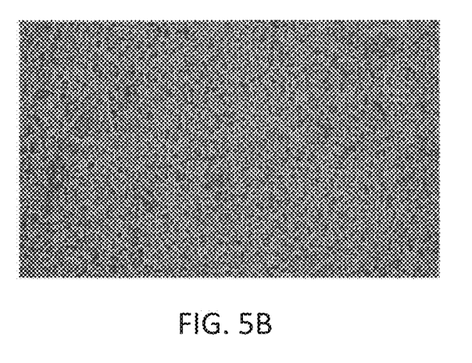
Figure 5C:
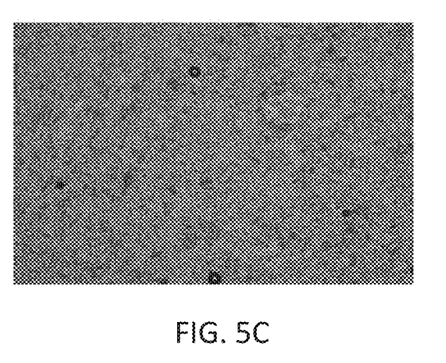

FIGS. 5A-5C show the formula of Example 3, herein, under increasing magnification (4×, 20×, and 10×, respectively), 24 hours after formulation. As is illustrated in these depictions, the dye system formulated according to Method II results in a dense consistency.

Figure 6A:
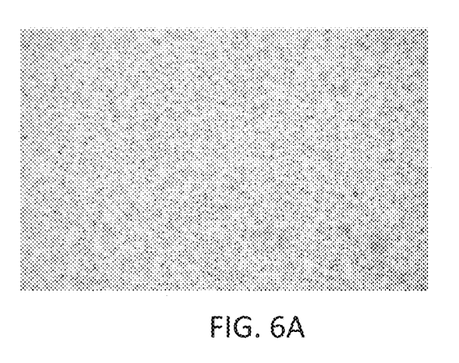
FIGS. 6A-6C show the formula of Example 4, when formulated according to Method III herein, under increasing magnification (4×, 20×, and 10×, respectively), 24 hours after formulation.
Figure 6B:
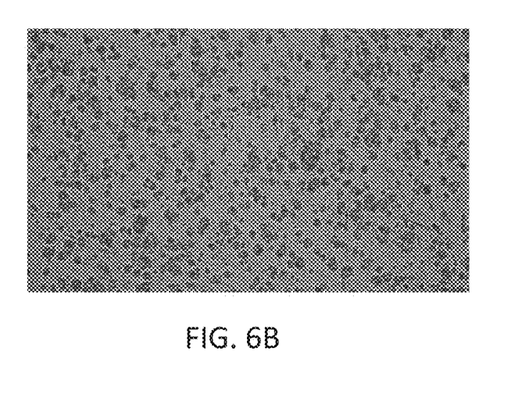
Figure 6C:
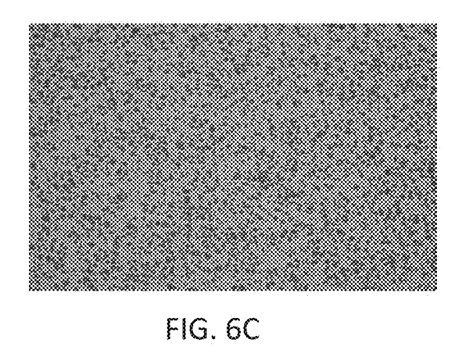

FIGS. 6A-6C show the formula of Example 4, under increasing magnification (4×, 20×, and 100×, respectively), 24 hours after formulation. As is illustrated in these depictions, the dye system formulated according to Method III results in a structure that generally conforms to the dye system depicted in FIGS. 3A-3C. Therefore, no thickening benefit results from application of Method III.

Figure 7A:
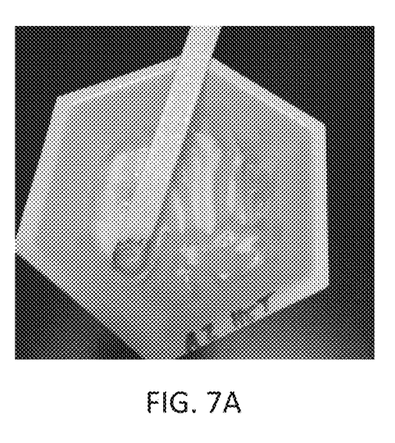
FIG. 7A is a photo of a sample composition according to Example 3, formulated according to Method II herein.
Figure 7B:
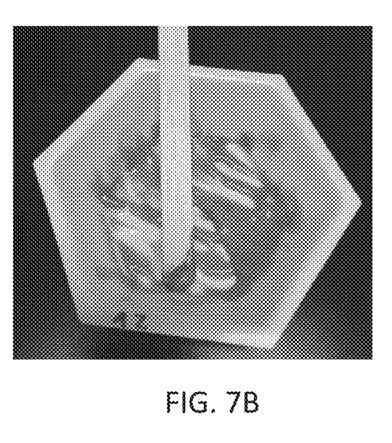
FIG. 7B is a photo of a sample composition according to Example 2, formulated according to Method I herein.
Figure 8A:
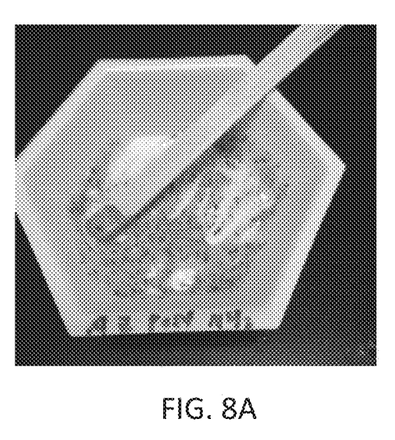
FIG. 8A is a photo of a sample composition according to Example 4, formulated according to Method III herein.
Figure 8B:
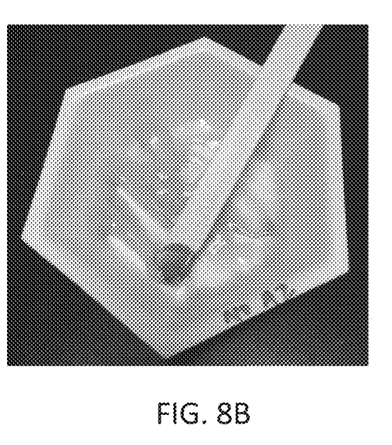
FIG. 8B is a photo of a sample composition according to Example 1.

FIGS. 7A, 7B, and 8B show the dye system having a homogeneous consistency. FIGS. 7A and 7B particularly show a thickened system, containing a homogeneous distribution of the catalyst herein.

In contrast, FIG. 8A shows a heterogeneous system, with interspersed clusters of the catalyst herein. This system results in an uneven distribution of the catalyst, creating catalytic "hot zones" with the system, which is unsuitable for controlled application of the catalyst system to hair. This further demonstrates the drawbacks of alkalizing the system before addition of the catalyst, as described by Method III herein.

Furthermore, in view of the enhanced rate of reaction achieved via the formulas herein, known sensitizers such as paraphenylenediamine (PPD) and paratoluenediamine (PTD) are not essential to the dye systems herein. Therefore, in one embodiment, the dye system herein is free from PPD or PTD.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A dye system for application to a substrate, said dye system comprising:
   (a) at least one dye precursor;
   (b) an oxidizing agent; and
   (c) a catalyst, wherein said dye system has a viscosity of less than about 2,500 mPa-s, when said viscosity is measured at a shear rate of about 25 $s^{-1}$ and at about 25° C.;
   wherein said dye system further comprises an alkalizer and wherein the dye system has a pH level of 9 and above.

2. The dye system of claim 1, wherein said substrate is human hair.

3. The dye system of claim 1, wherein said catalyst comprises at least one metal-containing compound.

4. The dye system of claim 3, wherein said catalyst comprises at least one inorganic metal compound.

5. The dye system of claim 4, wherein said inorganic metal compound is selected from the group consisting of at least one compound of a d-block transition metal, the salts of the alkali metals of Group 1, and the alkaline earth metals of Group 2.

6. The dye system of claim 3, wherein said d-block transition metal is selected from the group consisting of scandium, vanadium, chromium, molybdenum, iron, manganese, cobalt, nickel, copper, zirconium and zinc, or said alkali metal of Group 1 comprises potassium, or said alkaline earth metal of Group 2 comprises magnesium.

7. The dye system of claim 1, wherein said catalyst is aluminum zirconium glycinate.

8. The dye system of claim 1, wherein said alkalizer is selected from the group consisting of aminomethylpropanol, monoethanolamine, and ammonia.

9. The dye system of claim 1, wherein said dye precursor is free of 1,4-phenylenediamine, 1,4-toluenediamine, or combinations thereof.

* * * * *